United States Patent [19]

Zalewski

[11] 4,131,338
[45] Dec. 26, 1978

[54] MEASUREMENT OF INTERPUPILLARY DISTANCE

[76] Inventor: Henry M. Zalewski, 194 Washington Ave., Carteret, N.J. 07008

[21] Appl. No.: 799,954

[22] Filed: May 24, 1977

[51] Int. Cl.$^2$ .......................... A61B 3/10; A61B 3/04; A61B 3/00; G02C 11/02
[52] U.S. Cl. ................................. 351/5; 351/19; 351/39; 351/51
[58] Field of Search ................... 351/5, 19, 39, 51; 33/200

[56] References Cited

U.S. PATENT DOCUMENTS

| | | | |
|---|---|---|---|
| 1,505,447 | 8/1924 | Uhlemann | 351/5 |
| 1,555,388 | 9/1925 | Schumacher | 351/51 |
| 2,884,702 | 5/1959 | Engelmann | 33/200 |

*Primary Examiner*—Paul A. Sacher
*Assistant Examiner*—Rodney B. Bovernick
*Attorney, Agent, or Firm*—Charles E. Baxley

[57] ABSTRACT

Measurement of interpupillary distance is facilitated by providing a spectacle frame or the like to be worn by the optometrist, bearing at least two and preferably three indicia on said frame, in positions respectively adjacent the temples of the frame, and one centrally located adjacent the bridge. In measuring the interpupillary distance a preferred method, using the frame apparatus, is to instruct the patient to fix on one of the temporal indicia, and position the index or zero point, of an interpupillary rule directly in line with the center of the pupil on the same side as the indicium on which the patient is fixed. Then, without moving the rule, the optometrist instructs the patient to fix on the other temporal indicium, and reads from the rule the point opposite the pupil on that side. The interpupillary distance so measured corresponds substantially to the interpupillary distance at infinity — i.e. in the absence of convergence. For near-vision interpupillary distance, the patient is instructed to fix on the central indicium, while the optometrist positions his face at a position removed from the patient's face by substantially the patient's comfortable reading distance, and measures the center-to-center interpupillary distance.

2 Claims, 7 Drawing Figures

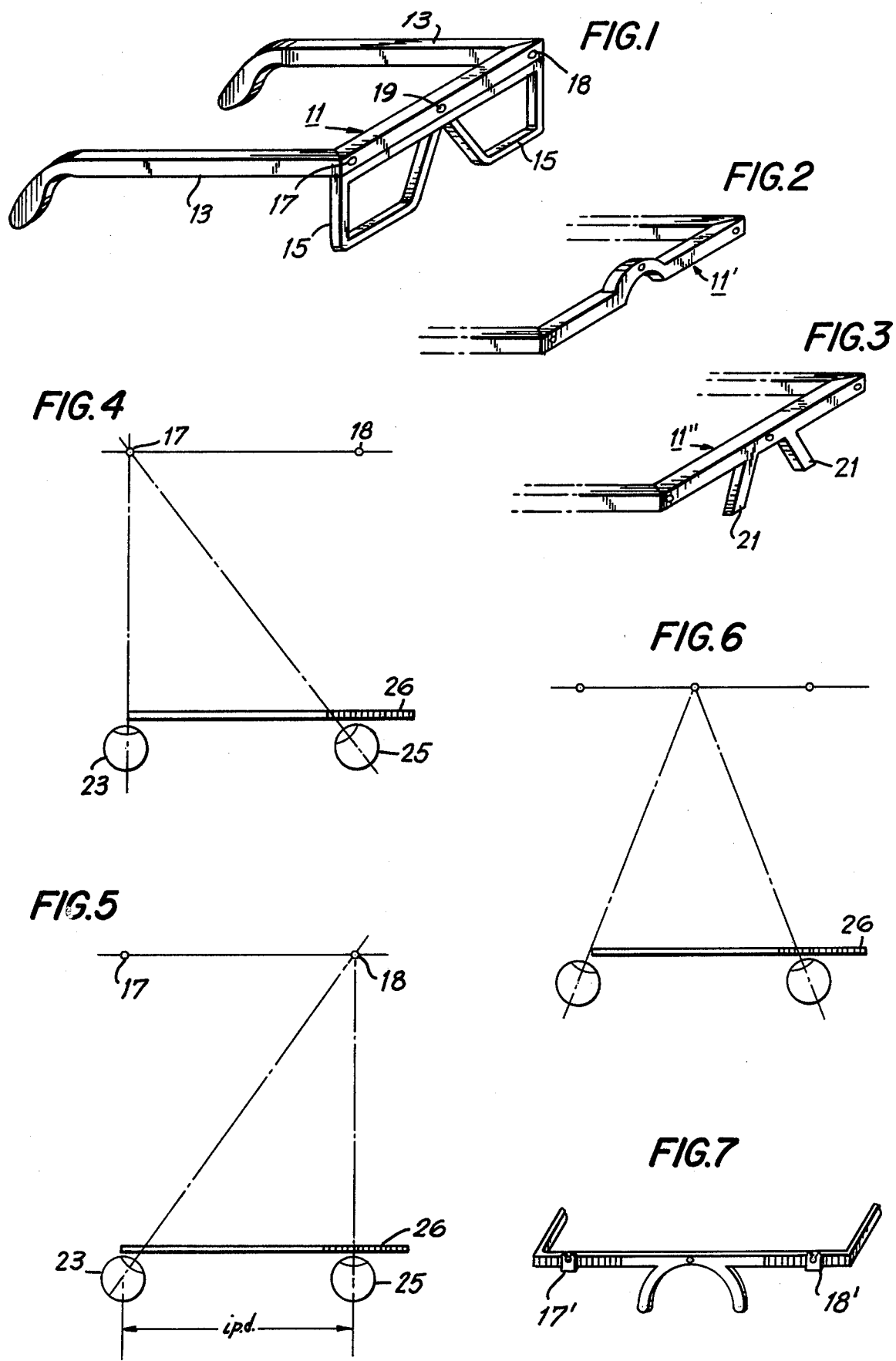

MEASUREMENT OF INTERPUPILLARY DISTANCE

BACKGROUND OF THE INVENTION

The importance, in fitting a patient with proper corrective spectacles, of accurate measurement of the interpupillary distance, has long been recognized. For example, Brown states: "The distance between the two eyes is a matter that should not escape the attention of the careful observer, because of the disturbing effect it may have on the act of convergence.

It seems like a very simple matter to measure the distance between the eyes, and yet when we inquire into the question carefully, we will find that to make an exact measurement is attended with no little difficulty.

In the first place, the pupil is not exactly in the center of the anterior part of the eye-ball, The second element of error lies in the difficulty of measuring the exact distance between the pupils, as this is a point that can only be determined approximately." (C. H. Brown, M.D., "The Optician's Manual", Publ. by The Keystone, Philadelphia, Copr. 1897, pp. 187-188).

The significance of the interpupillary distance is that it determines the distance between the optical axes of the two eyeballs. In any corrective lens, it is important that the optic axis of the lens (or portion thereof, in the case of bifocal or multifocal lenses) coincide with the optic axis of the eyeball before which it is placed. Otherwise, a prismatic error is introduced, in that, in order to fix upon an object, the eye is constrained to fix slightly off-center, rather than directly through the optical center of the lens. As a result, a prismatic error is introduced as a ray of light from the object passes angularly (instead of normal) to the surface of the optically denser medium of the lens, and a second error, of opposite sign, when the ray emerges from the dense medium of the lens to the less dense medium of the atmosphere between the lens and the eyeball. When the lens approaches a biplanar surface, as in lenses of less than 1 diopter strength, the two errors tend to cancel each other, and no serious problem is introduced. When stronger lenses are involved, however, the opposed lens surfaces depart more and more from the configuration of two parallel planes, and the residual, uncancelled prismatic errors may become quite serious. For example the New Jersey State Board of Opticians, for purposes of its qualifying examination, accepts a prismatic error of no greater than plus or minus 0.25 prism diopters in each lens. Considering that existing methods of measuring interpupillary distance commonly introduce errors of plus or minus 4 mm. in interpupillary distance, taken together with the fact that an error as small as 1 mm., in measurement of interpupillary distance for a plus 5 diopter corrective lens, introduces a prismatic error of 0.5 prism diopters (sometimes indicated by the notation 0.5° prism), it can readily be seen that large and unacceptable errors are readily introduced by faulty measurement of interpupillary distance.

The quantity "prism" or "prism diopters" is the displacement in millimeters of an image on a screen 1 meter away from the lens, cast through the lens by a point source of light on the optical axis of the lens located 1 meter from the lens on the side opposite the screen.

Thus, in addition to the strain on the recti muscles used for convergence, when the optical axis of the lens fails to coincide with that of the eye, there is an additional disadvantage, resulting from distortion introduced by prismatic error. In extreme cases, prismatic error may result in unsharpness and color fringes, based on the prismatic dispersion of light of different wavelengths, in the same manner as in a Newtonian prism.

OBJECTIVES OF THE INVENTION

An object of this invention, therefore, is to provide an improved method and apparatus for measuring interpupillary distances.

Another object is to provide a method and apparatus for measurement of interpupillary distances with improved accuracy.

Still another object is to provide an apparatus for facilitating interpupillary measurements which is simple and inexpensive to manufacture, and equally simple to use.

Yet another object is to provide such apparatus, which is unobtrusive and can be used for general wear as a pair of spectacles for street wear and between examinations.

Other objects and advantages will become apparent from the following more complete description and claims, taken together with the accompanying drawings.

BRIEF DESCRIPTION OF THE DRAWINGS

FIG. 1 of the drawings is a perspective view of one embodiment of the apparatus according to the invention.

FIG. 2 is a fragmentary perspective view similar to a portion of FIG. 1 showing an alternative embodiment of the apparatus.

FIG. 3 is a fragmentary perspective view, similar to FIG. 2, showing another alternative form of the apparatus.

FIG. 4 is a diagrammatic plan view, showing a first step in the determination of distant vision interpupillary distance.

FIG. 5 is a diagrammatic plan view, showing a second step in the determination of distant vision interpupillary distance.

FIG. 6 is a diagrammatic plan view illustrating the method of determining near vision interpupillary distance using the apparatus according to the invention.

FIG. 7 is a front elevation of another alternative form of the apparatus of the invention, particularly suitable where it is required to measure distant vision interpupillary distance with a high degree of accuracy, as where powerful corrective lenses, for example 4 to 5 diopters or stronger, are to be used.

BRIEF STATEMENT OF THE INVENTION

The foregoing and other objects of the invention are accomplished by the present invention, which contemplates apparatus for facilitating measurement of interpupillary distance, said apparatus comprising in combination:

a frame provided with a horizontal bar and means for holding said bar in fixed position adjacent the face of the user adjacent said user's eyes, said horizontal bar bearing a plurality of indicia suitable to be fixed upon by a patient, one of said indicia being disposed adjacent each of the respective temples of the user.

This invention also contemplates a method of measuring distant vision interpupillary distance of a patient, comprising in combination the steps of:

fixing the patient's vision on a first indicium located adjacent one of the use's temples, establishing, as a zero point, a point directly before the center of the patient's pupil on the same side as said first indicium, fixing the patient's vision on the second indicium located adjacent the other of said user's temples, noting, as a measurement point, a point directly before the center of the patient's pupil on the same side as said second indicium, and taking, as the distant vision interpupillary distance, the lateral distance between said zero point and said measurement point.

DESCRIPTION OF PREFERRED EMBODIMENTS

Referring now more particularly to the preferred embodiments as illustrated in the drawings, FIG. 1 shows an embodiment in which the apparatus is combined with a pair of spectacle frames, including a horizontal bar 11 connected at its ends in conventional manner to temple pieces 13,13 and forming the upper margin of lens frames 15,15. Horizontal bar 11 is provided with temporal indicia 17,18, adjacent the points at which the horizontal bar is connected to temple pieces 13,13, respectively. Horizontal bar 11 is also provided centrally intermediate its extremities, in the vicinity of the nasal bridge, with a third indicium 19. Indicia 17,18 and 19 are shown in FIG. 1 as small inserts of a material of color contrasting with the basic color of horizontal bar 11. In this embodiment, the indicia are relatively unobtrusive and do not interfere with the use of the apparatus as ordinary spectacles for street wear. If desired, they may be made more prominent, by substituting reflective elements, rhinestones or the like for the colored inserts, or may be in the form of miniature electric lights, controlled by individual switches, as will be readily apparent to those skilled in the art.

FIG. 2 illustrates an alternative embodiment, in which horizontal bar 11' is bowed upwardly in the center to provide a curved recess for the bridge of the user's nose, thereby locating the horizontal bar in a predetermined position with respect to the user's face. FIG. 2 also shows that the apparatus need not be provided with spectacle lenses, in cases where the user does not require visual correction (or where it is accomplished, e.g., by the use of contact lenses).

FIG. 3 shown another alternative similar to FIG. 2, except that instead of an upward bow in the horizontal bar, the horizontal bar 11" is provided with a pair of dependent extensions 21,21 which cooperate to define a nose bridge for reception of the upper part of the user's nose.

FIGS. 4 and 5, taken together, illustrate the method of measuring the patient's distant vision interpupillary distance. It will be understood that the angular displacements in these diagrammatic views (including FIG. 6) are greately exaggerated for the purpose of clarity of illustration.

In the performance of the measurement as illustrated in FIGS. 4 and 5, the patient is positioned in facing relationship to the apparatus as illustrated in FIGS. 1, 2 or 3, so that indicia 17,18 are respectively in front of the left and right eyeballs, respectively designated 23 and 25, of the patient. The patient is then instructed to look at one of the indicia, for example indicium 17, (opposite eyeball 23). While the patient maintains this orientation, the user places an interpupillary rule 26 (or an ordinary millimeter rule) before eyeball 23, in such a way that the zero point of the rule (or any selected marking on the rule) is directly in front of the center of the pupil of eyeball 23. Without moving the rule, the user then instructs the patient to look at the other temporal indicium – i.e. indicium 18, before the other eyeball (25), and notes the point on the rule which is directly in front of the pupil of eyeball 25. The distance between the zero point as noted in the first step and measurement point as noted in the second step is taken as the patient's distant vision interpupillary distance – i.e. the distance between the pupils in the absence of convergence.

The measurement as just described depends on the assumption that the patient's interpupillary distance for distant vision approximates the horizontal distance between indicia 17 and 18, so that the direction of a light ray from indicium 17 to eyeball 23 is parallel with that of a light ray from indicium 18 to eyeball 25. This is ordinarily a fair approximation. However, for especially critical measurement, 11 should be noted that if the indicia are spaced apart by slightly less than the patient's distant vision interpupilary distance, the resulting measurement will be slightly inaccurate in that the two rays which should be parallel will show some residual convergence, whereas if indicia 17 and 18 are spaced too far apart the indicated measurement will show a divergent error — as if the patient were slightly exotropic or "wall-eyed". For critical measurements, therefore, it is desirable to further refine the accuracy of the method. This may be done using an embodiment of the apparatus as illustrated in FIG. 7.

The apparatus as shown in FIG. 7 is similar to those shown in the other alternative embodiments (that of FIG. 3 has been selected for illustration), except that the temporal indicia 17', 18' are movable along the length of bar 11.

To make a particularly accurate measurement of distant vision interpupillary distance using the apparatus as shown in FIG. 7, a preliminary measurement of that quantity is made as already described, and movable indicia 17' and 18' are so adjusted, using integral graduated scales marked on horizontal bar 11, so that each of the movable indicia 17' and 18' is spaced from the center of the bar by one-half the amount of the interpupillary distance as preliminarily measured. The determination is then repeated, using the so-positioned indicia 17' and 18'. The resulting quantity is a highly accurate measurement of the interpupillary distance for extreme distant vision, i.e. in the substantial absence of any convergence.

It may be noted that this method of measurement is also applicable to patients suffering from esotropia or exotropia — conditions which normally introduce considerable complications into the measurement of distant vision interpupillary distances. In such cases, it may be advisable to cover the eye not under consideration, to prevent erroneous results resulting from the tendency to fix the dominant eye on the object, overriding the normal tendency to fix both eyes on the object by normal convergence of the ocular optic axes.

FIG. 6 illustrates diagrammatically the method of determining the near vision interpupillary distance using the apparatus according to this invention. The optometrist, wearing the apparatus according to this invention, faces the patient directly, at a normal comfortable reading distance — about 1½ feet - and instructs him to look at the central indicium 19. While the patient is fixed upon the central indicium, the optometrist places the end or a designated mark on an interpupillary rule or millimeter rule 26 opposite the center of one pupil, and notes the point on the rule which is directly before the center of the other pupil. The lateral spacing between the two readings is the near vision interpupillary distance.

While this invention has been described in terms of certain preferred embodiments and illustrated by way of certain drawings, these are illustrative only, as many alternatives and equivalents will readily occur to skilled in the art, and the invention is not to be construed as limited, except as set forth in the appended claims.

I claim:

1. A method of measuring distant vision interpupillary distance, comprising in combination the steps of:
    fixing the patient's vision on a first indicium located adjacent one of the user's temples,
    establishing, as a zero point, a point directly before the center of the patient's pupil on the same side as said first indicium,
    fixing the patient's vision on a second indicium located adjacent the other of said user's temples,
    noting, as a measurement point, a point directly before the center of the patient's pupil on the same side as said second indicium, and
    taking, as the distant vision interpupillary distance, the lateral distance between said zero point and said measurement point.

2. A method according to claim 1, further comprising the steps of taking the distant vision interpupillary distance as determined according to claim 1 as a preliminary measurement, setting said first and second indicia at positions equidistant from a central point adjacent the nasal bridge of the user, and separated from each other by a total distance equal to the interpupillary distance as determined by the method according to claim 4, and repeating the steps recited in claim 4, thereby obtaining a second and more accurate measurement of the patient's distant vision interpupillary distance.

* * * * *

UNITED STATES PATENT AND TRADEMARK OFFICE
CERTIFICATE OF CORRECTION

PATENT NO.  : 4,131,338
DATED       : December 26, 1978
INVENTOR(S) : Henry M. Zalewski It is certified that error appears in the above-identified patent and that said Letters Patent are hereby corrected as shown below:

Column 6, line 19, delete [claim 4] and insert
  claim 1 therefor;

line 20, delete [claim 4] and insert
  claim 1 therefor.

Signed and Sealed this

Fifth Day of June 1979

[SEAL]

Attest:

RUTH C. MASON
Attesting Officer

DONALD W. BANNER
Commissioner of Patents and Trademarks